(12) United States Patent
Schoonover et al.

(10) Patent No.: US 12,390,573 B2
(45) Date of Patent: Aug. 19, 2025

(54) SYSTEM AND METHODS FOR AUTOMATIC DILUTION OF WHOLE BLOOD TO INCREASE PLASMA CLARITY

(71) Applicant: Fenwal, Inc., Lake Zurich, IL (US)

(72) Inventors: Matthew J. Schoonover, Chicago, IL (US); Jeffrey R. Maher, Schaumburg, IL (US)

(73) Assignee: Fenwal, Inc., Lake Zurich, IL (US)

( * ) Notice: Subject to any disclaimer, the term of this patent is extended or adjusted under 35 U.S.C. 154(b) by 134 days.

(21) Appl. No.: 16/984,320

(22) Filed: Aug. 4, 2020

(65) Prior Publication Data

US 2021/0052805 A1 Feb. 25, 2021

Related U.S. Application Data

(60) Provisional application No. 62/889,245, filed on Aug. 20, 2019.

(51) Int. Cl.
*A61M 1/36* (2006.01)
*A61M 1/30* (2006.01)

(52) U.S. Cl.
CPC .......... *A61M 1/3693* (2013.01); *A61M 1/308* (2014.02); *A61M 1/361* (2014.02);
(Continued)

(58) Field of Classification Search
CPC .... A61M 1/3693; A61M 1/308; A61M 1/361; A61M 1/3612; A61M 1/3673; A61M 1/16; A61M 1/303; A61M 1/3609; A61M 1/3644; A61M 1/3643; A61M 1/30; A61M 1/3496; A61M 2202/0429; A61M 2205/12; A61M 2205/50; A61M 2240/00; A61M 1/3692; A61M 1/3672; A61M 1/3406; A61M 1/341; A61M 1/34; A61M 1/72; A61M 1/73; A61M 1/342; A61M 1/3424;
(Continued)

(56) References Cited

U.S. PATENT DOCUMENTS 5,200,090 A * 4/1993 Ford ................... A61M 1/3451
210/135
5,316,667 A 5/1994 Brown et al.
(Continued)

FOREIGN PATENT DOCUMENTS

WO WO-9611747 A2 * 4/1996 .......... A61M 1/3692

*Primary Examiner* — Akash K Varma
(74) *Attorney, Agent, or Firm* — Cook Alex Ltd.

(57) ABSTRACT

A method and device are provided for centrifugally separating plasma from whole blood in which whole blood is introduced into a flow circuit having a blood access device connected to a first tubing for drawing whole blood from a blood source and for flowing whole blood to a centrifugal separation chamber; a volume of saline is added to the whole blood as it flows through the first tubing to dilute the whole blood; the volume of saline added to the whole blood is tracked; the whole blood having saline added thereto is separated in the centrifugal separation chamber so that an interface is created between the plasma and added saline and the cellular components of the whole blood; the separated plasma and added saline is flowed from the centrifugal separation chamber to a collection container; and a volume for the plasma and added saline in the collection container is determined.

10 Claims, 4 Drawing Sheets

(52) U.S. Cl.
CPC ........ *A61M 1/3612* (2014.02); *A61M 1/3622* (2022.05); *A61M 1/36222* (2022.05); *A61M 1/36225* (2022.05); *A61M 1/3673* (2014.02); A61M 2205/50 (2013.01)

(58) Field of Classification Search
CPC .............. A61M 1/3696; A61M 1/3695; A61M 1/3698; A61M 1/3646; A61M 1/382; A61M 1/385; A61M 1/38; A61M 2205/128; A61M 2205/33; A61M 2205/3306; A61M 2205/331; A61M 2205/502; A61M 2205/505; A61M 2202/04; A61M 2202/0415; A61M 2202/0468; B01D 17/0217
USPC ........................................................ 210/787
See application file for complete search history.

(56) References Cited

U.S. PATENT DOCUMENTS

| | | | |
|---|---|---|---|
| 5,868,696 A | 2/1999 | Giesler et al. | |
| 5,939,319 A * | 8/1999 | Hlavinka | B04B 5/0428 435/372 |
| 6,027,657 A | 2/2000 | Min et al. | |
| 6,723,062 B1 * | 4/2004 | Westberg | A61M 1/30 604/4.01 |
| 8,858,488 B2 * | 10/2014 | Kelly | A61M 1/3626 604/6.11 |
| 9,119,914 B2 * | 9/2015 | Nguyen | A61M 1/3644 |
| 9,164,078 B2 | 10/2015 | Min et al. | |
| 9,533,089 B2 | 1/2017 | Min et al. | |
| 9,629,951 B2 * | 4/2017 | Delmage | A61M 1/3403 |
| 9,943,638 B2 | 4/2018 | Min et al. | |
| 10,376,620 B2 * | 8/2019 | Lynn | A61M 1/34 |
| 2004/0147865 A1 * | 7/2004 | Cianci | A61M 1/3693 494/37 |
| 2006/0155236 A1 * | 7/2006 | Gara | A61M 1/3686 604/4.01 |
| 2009/0211987 A1 * | 8/2009 | Min | A61M 1/3612 210/744 |
| 2015/0320925 A1 * | 11/2015 | Ali | A61M 1/342 422/44 |
| 2016/0175514 A1 * | 6/2016 | Thill | G01N 33/491 702/25 |
| 2018/0078696 A1 * | 3/2018 | Abedin | A61M 1/38 |
| 2018/0361054 A1 * | 12/2018 | Roxas | A61M 1/367 |
| 2019/0313953 A1 * | 10/2019 | Kusters | A61B 5/1455 |
| 2020/0166451 A1 * | 5/2020 | Kusters | G01N 21/251 |
| 2020/0338252 A1 * | 10/2020 | Ali | A61M 1/85 |
| 2020/0384482 A1 * | 12/2020 | Kusters | A61M 1/3603 |

* cited by examiner

SYSTEM AND METHODS FOR AUTOMATIC DILUTION OF WHOLE BLOOD TO INCREASE PLASMA CLARITY

TECHNICAL FIELD

The disclosure relates to blood treatment systems and methods. More particularly, the disclosure relates to systems and methods for separating blood into its constituents by centrifugation.

BACKGROUND

Various blood processing systems now make it possible to collect particular blood constituents, rather than whole blood, from donors or patients. Typically, in such systems, whole blood is drawn from a donor, the particular blood component or constituent is removed and collected, and the remaining blood constituents are returned to the donor. By thus removing only particular constituents, potentially less time is needed for the donor's body to return to pre-donation levels, and donations can be made at more frequent intervals than when whole blood is collected. This increases the overall supply of blood constituents, such as plasma and platelets, made available for health care.

Whole blood is commonly separated into its constituents through centrifugation. This requires that the whole blood be passed through a centrifuge after it is withdrawn from, and before it is returned to, the donor. To avoid contamination and possible infection of the donor, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid circuit that is mounted in cooperation on the hardware. The centrifuge assembly engages and spins a separation chamber of the disposable fluid circuit during a blood separation step. The blood, however, makes actual contact only with the fluid circuit, which assembly is used only once and then discarded.

As the whole blood is spun by the centrifuge, an interface is created between the blood components having different specific gravities, with the heavier (greater specific gravity) components, such as red blood cells, move radially outwardly away from the center of rotation toward the outer or "high-G" wall of the separation chamber of the fluid circuit and the lighter (lower specific gravity) components, such as plasma, migrating toward the inner or "low-G" wall of the separation chamber. Various ones of these blood components can be selectively removed from the whole blood through appropriately located channeling seals and outlet ports in the separation chamber of the fluid circuit. For example, one application of therapeutic plasma exchange involves separating plasma from cellular blood components, collecting the plasma, and returning the cellular blood components and a replacement fluid to the donor.

The ability to determine the interface between the RBC layer and the plasma layer is important for achieving efficient separation. If the whole blood being separated is moderately or highly lipemic (i.e., contains fat), the plasma becomes cloudy, and it is difficult for the optical sensors to accurately identify the separation interface. Further, in therapeutic apheresis, the medications that the patients are taking may also have an impact on plasma clarity resulting in similar conditions described above with lipemic plasma. The inability to accurately identify the actual RBC and plasma separation interface decreases the efficiency of the procedure and can prevent a procedure from being completed. To mitigate the probability of incomplete or inefficient procedures, Operators sometimes infuse the patient with saline either prior to or during the apheresis procedure in order to dilute the plasma to make it less turbid. However, because this dilution is not controlled, it changes the input parameters of the whole blood, such as the patient hematocrit and total blood volume, which creates other problems in performing the procedure.

Accordingly, by way of the present disclosure systems and methods are provided for automatically diluting the whole blood as it enters the separation system, so that there is more control over the manner in which the whole blood is diluted and the amount of diluent that is added to the system, and to automatically account for the changes in donor parameters, such as hematocrit or total blood volume, procedure endpoint targeting, and predicted procedure outputs for the patient.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately, or the claiming of such aspects separately or in different combinations as set forth in the claims appended hereto.

In a first aspect, a method for centrifugally separating plasma from whole blood is provided comprising: a) introducing anticoagulated whole blood into a flow circuit having a blood access device connected to a first tubing for drawing whole blood from a blood source, mixing with anticoagulant, and for flowing whole blood to a centrifugal separation chamber; b) adding a volume of saline to the whole blood as it flows through the first tubing to dilute the whole blood; c) tracking the volume of saline added to the whole blood; d) separating the whole blood having the volume of saline added thereto in the centrifugal separation chamber whereby an interface is created between the plasma and added saline and the cellular components of the whole blood; e) flowing the separated plasma and added saline from the centrifugal separation chamber to a collection container; and f) determining a volume for the plasma and added saline in the collection container.

In a second aspect, a device for separating plasma from whole blood is provided comprising: a) a reusable hardware component comprising a centrifuge, an interface detector associated with the centrifuge, at least one pump, a first weigh scale, a second weigh scale, and a programmable controller for automatically operating the device; b) a single-use fluid flow circuit mounted to the reusable hardware component comprising a blood source access device, a separation chamber configured to be received in the centrifuge, first tubing segment connected on a first end to the blood source access device and on a second end to the separation chamber, a container of saline supported by the first weigh scale, a second tubing segment associated with the pump connected on a first end to the container of saline and on a second end to the first tubing segment, a collection container supported by the second weigh scale, and a third tubing segment connected on a first end to the separation chamber and on a second end to the collection container. The programmable controller is configured to: i) operate the first pump to flow saline from the container of saline through the second tubing segment to the first tubing segment to dilute the whole blood flowing through the first tubing segment, ii) track a volume of saline flowed from the container of saline through the second tubing segment to the first tubing segment, and iii) flow separated plasma and added saline from the separation chamber through the third tubing segment to the collection container, and iv) determine a volume for the plasma and added saline in the collection container.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
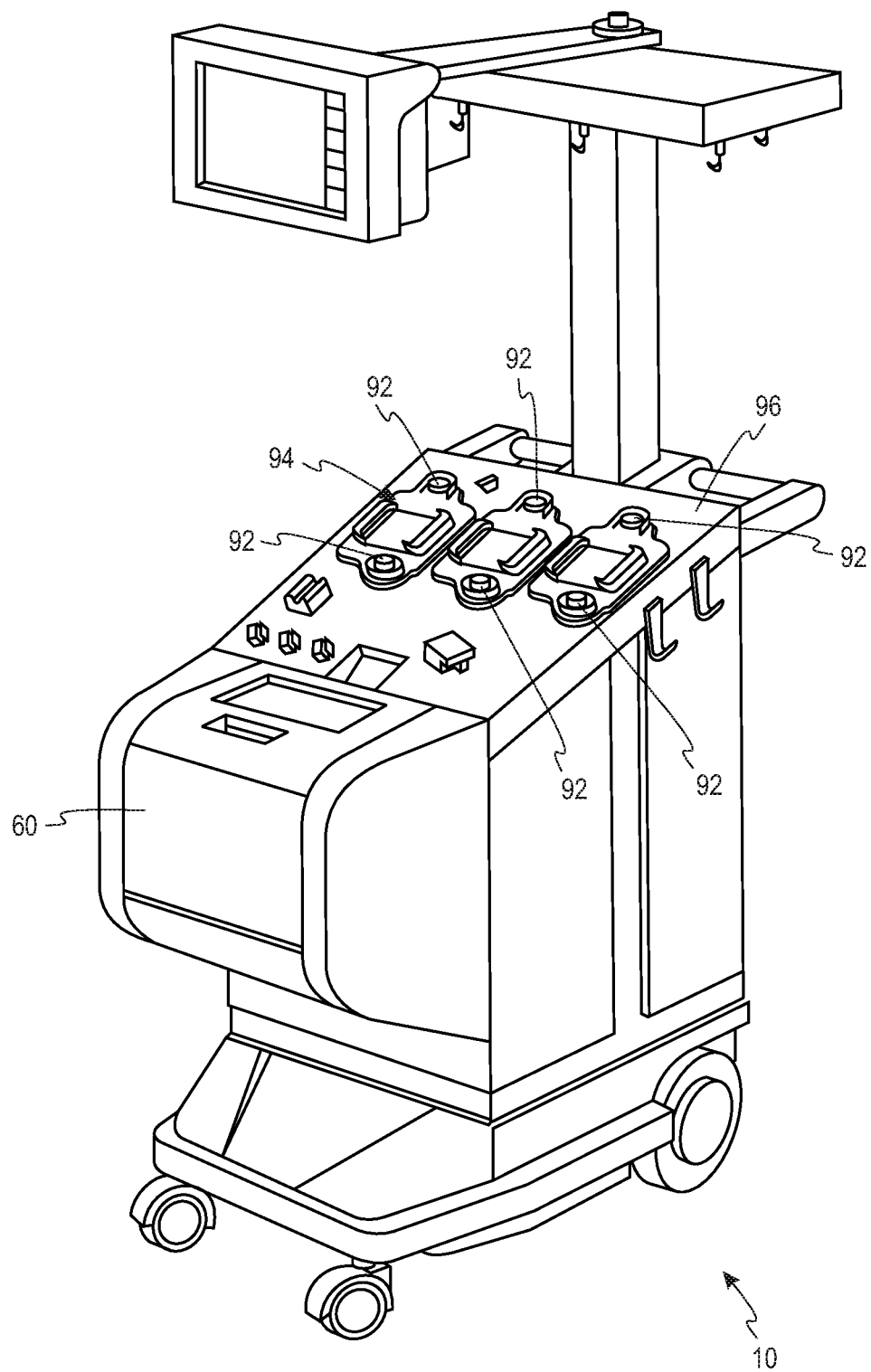
FIG. 1 is a perspective view of an exemplary fluid processing system of a blood separation system that may be used in combination with a disposable flow circuit, in accordance with an aspect of the present disclosure.

FIG. 1 shows an exemplary durable/reusable fluid processing system 10 which is suitable for use according to aspects of the present disclosure. The fluid processing system 10 may be provided generally according to known design, such as the system currently marketed as the AMICUS® separator by Fenwal, Inc. of Lake Zurich, Ill., as described in greater detail in U.S. Pat. No. 5,868,696, which is hereby incorporated herein by reference. The system 10 can be used for processing various fluids, but is particularly well suited for processing whole blood, blood components, or other suspensions of biological cellular materials.

Figure 2:
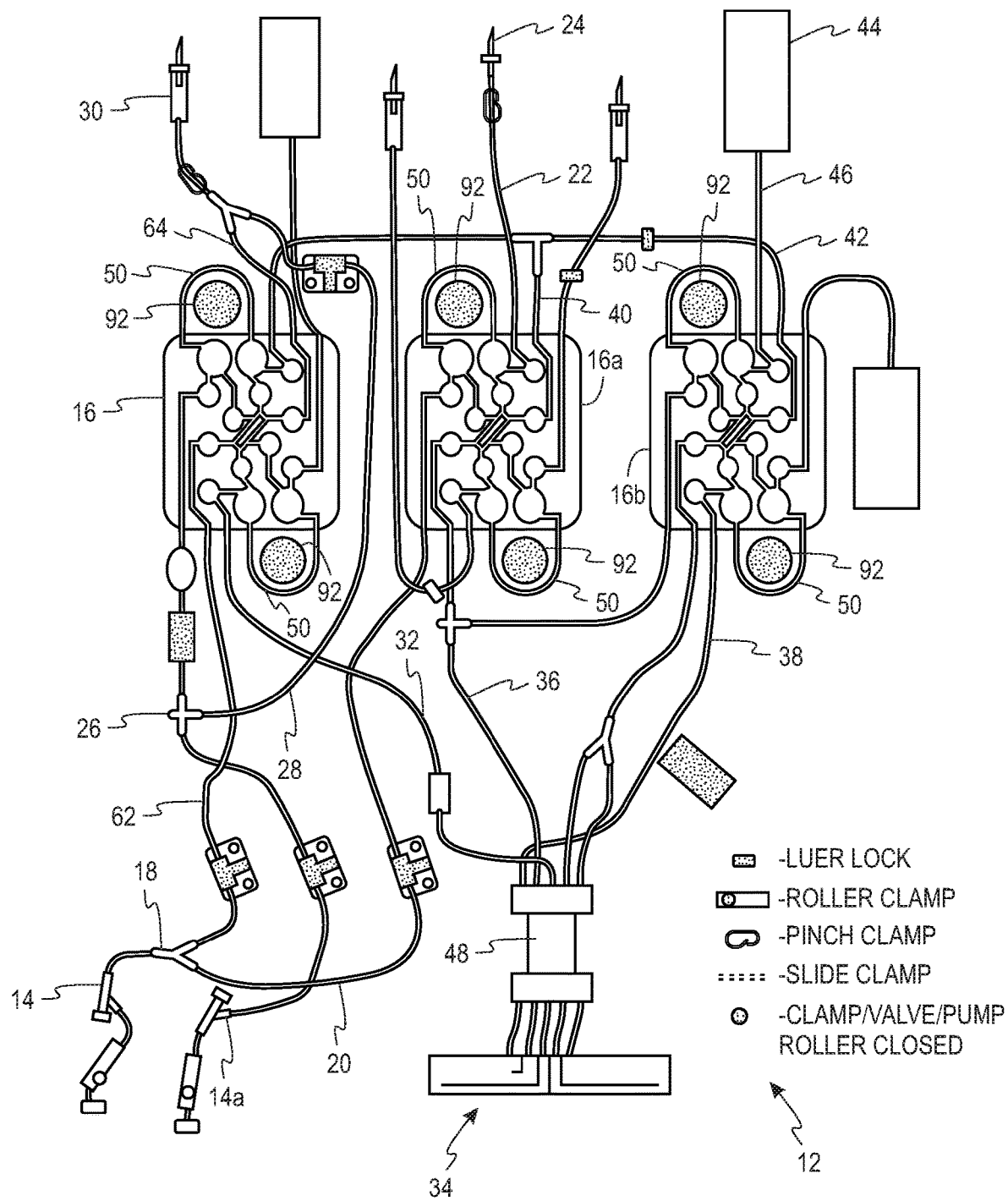
FIG. 2 is a diagrammatic view of an exemplary disposable flow circuit that may be used in combination with the fluid processing system of FIG. 1.

The fluid processing system 10 is used in combination with a single-use flow circuit 12, such as the one illustrated in FIG. 2, to form a centrifugation system. The flow circuit 12 includes a number of tubing segments and components, only some of which will be described herein in greater detail. The flow circuit 12 of FIG. 2 is specially configured to be used in combination with the fluid processing system 10 of FIG. 1, but it should be understood that the flow circuit may be differently configured if the fluid processing system is differently configured from the embodiment of FIG. 1.

The illustrated flow circuit 12 is a "two needle" system, which includes a pair of blood source access devices 14 and 14a (e.g., phlebotomy needles) for fluid connecting a blood source with the flow circuit 12. The blood source access devices 14 and 14a are connected by tubing to a left cassette 16, which will be described in greater detail herein. One of the blood source access devices 14 is used to draw blood from the blood source into the flow circuit 12 and is connected to the left cassette 16 by a y-connector 18. The other leg of the y-connector 18 is connected to tubing 20 which leads to a middle cassette 16a. The tubing 20 is connected, through the middle cassette 16a, to additional tubing 22, which includes a container access device 24 (e.g., a sharpened cannula or spike connector) for accessing the interior of an anticoagulant container (not illustrated). During a blood treatment operation, anticoagulant from the anticoagulant container is added to the blood from the blood source at the y-connector 18 prior to entering the left cassette 16.

The other blood source access device 14a is used to deliver or return blood, a blood component, and/or some other replacement fluid to the blood source and is also connected to the left cassette 16 by a t-connector 26. The other leg of the t-connector 26 is connected to tubing 28 connected at its other end to a container access device 30. Although not illustrated, the container access device 30 may be associated with a container having an amount of fluid (e.g., saline) to be used to prime the flow circuit 12, delivered to the blood source via the blood source access device 14a, and/or added to the blood prior to centrifugation, as will be described in greater detail below.

The left cassette 16 also includes tubing 32 which is connected to a blood separation chamber 34 of the flow circuit 12 for flowing anticoagulated blood thereto. The blood separation chamber 34 separates the blood into its constituent parts and returns the blood components to the flow circuit 12. In one embodiment, cellular blood components are returned to the middle cassette 16a of the flow circuit 12 from the blood separation chamber 34 via tubing 36, while substantially cell-free plasma is returned to a right cassette 16b of the flow circuit 12 from the blood separation chamber 34 via tubing 38. The cellular blood components may be pumped to the left cassette 16 via tubing 40, where they are returned to the blood source. The plasma may be pumped back to the left cassette 16 via tubing 42 for return to the blood source and/or it may be pumped into a container 44 via different tubing 46. The destination of the plasma (and the other fluids passing through the cassettes) depends upon the actuation of the various valves of the cassettes, as will be described in greater detail herein. The various tubings connected to the blood separation chamber 34 are bundled in an umbilicus 48.

Additional tubing may be connected from one port of a cassette to another port of the same cassette, so as to form tubing loops 50 which interact with a fluid flow element or pump to flow fluid through the flow circuit 12.

The fluid processing system 10 includes a centrifuge 52 (FIGS. 3 and 4) used to centrifugally separate blood components. The fluid processing system 10 may be programmed to separate blood into a variety of components (e.g., platelet-rich plasma and red cells). For illustrative purposes, a therapeutic plasma exchange procedure, in which the centrifuge 52 separates whole blood into cellular components (e.g., red blood cells and platelets) and substantially cell-free plasma, will be described herein. However, the principles described and claimed herein may be employed with other blood separation procedures without departing from the scope of the present disclosure.

The illustrated centrifuge 52 is generally of the type shown in U.S. Pat. No. 5,316,667 to Brown et al., which is incorporated herein by reference. The centrifuge 52 comprises a bowl 54 and a spool 56. The bowl 54 and spool 56 are pivoted on a yoke 58 between an operating position (FIG. 3) and a loading/unloading position (FIG. 4). The centrifuge 52 is housed within the interior of the fluid processing system 10, so a door 60 is provided to allow access to the centrifuge 52 for loading and unloading the blood separation chamber 34, as will be described in greater detail herein. The door 60 remains closed during operation to protect and enclose the centrifuge 52.

When in the loading/unloading position, the spool 56 can be opened by movement at least partially out of the bowl 54, as FIG. 4 shows. In this position, the operator wraps the flexible blood separation chamber 34 about the spool 56. Closure of the spool 56 and bowl 54 encloses the chamber 34 for processing. When closed, the spool 56 and bowl 54 are pivoted into the operating position of FIG. 3 for rotation about a central rotational axis.

Blood entering the blood separation chamber 34 is pumped thereinto by one or more pumps 92 of the fluid processing system 10 (FIGS. 1 and 2) acting upon one or more of the tubing loops 50 extending from the cassettes 16-16*b* of the flow circuit 12 (FIG. 2).

Before beginning a given blood processing and collection procedure, the operator loads various components of the flow circuit 12 onto the sloped front panel 96 and centrifuge 52 of the fluid processing system 10. The front panel 96 preferably includes a hematocrit detector sensor 51 to be associated with the tubing from the blood access device 14 for determining the hematocrit of the whole blood as it is introduced into the flow circuit 12. The hematocrit sensor may comprise an infrared (IR) light source and an optical sensor, such as that described in U.S. Pat. No. 9,164,078, incorporated herein by reference.

Figure 3:
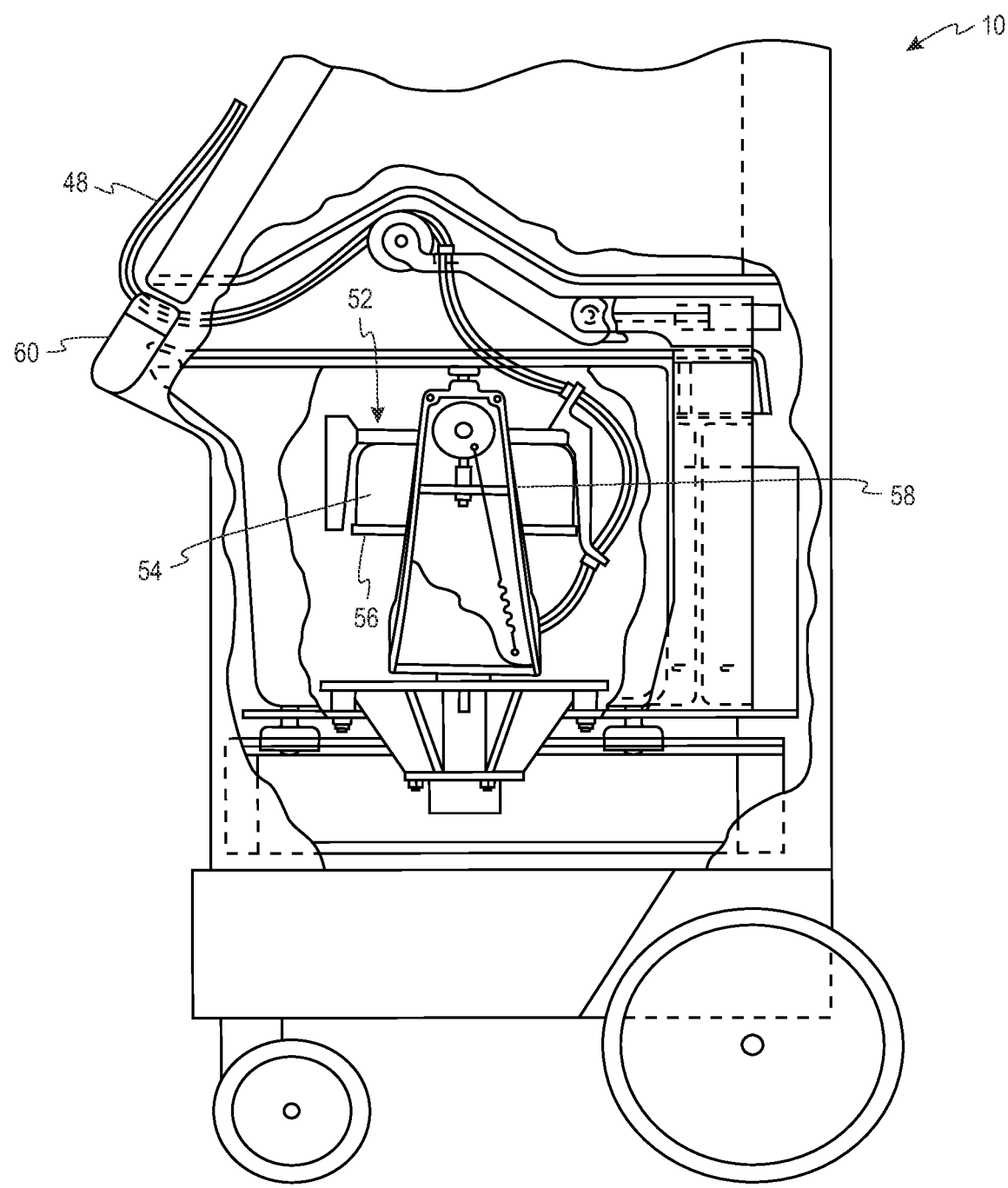
FIG. 3 is a side elevational view, with portions broken away and in section, of the fluid processing system of FIG. 1, with a centrifuge bowl and spool of the system being shown in their operating position.
Figure 4:
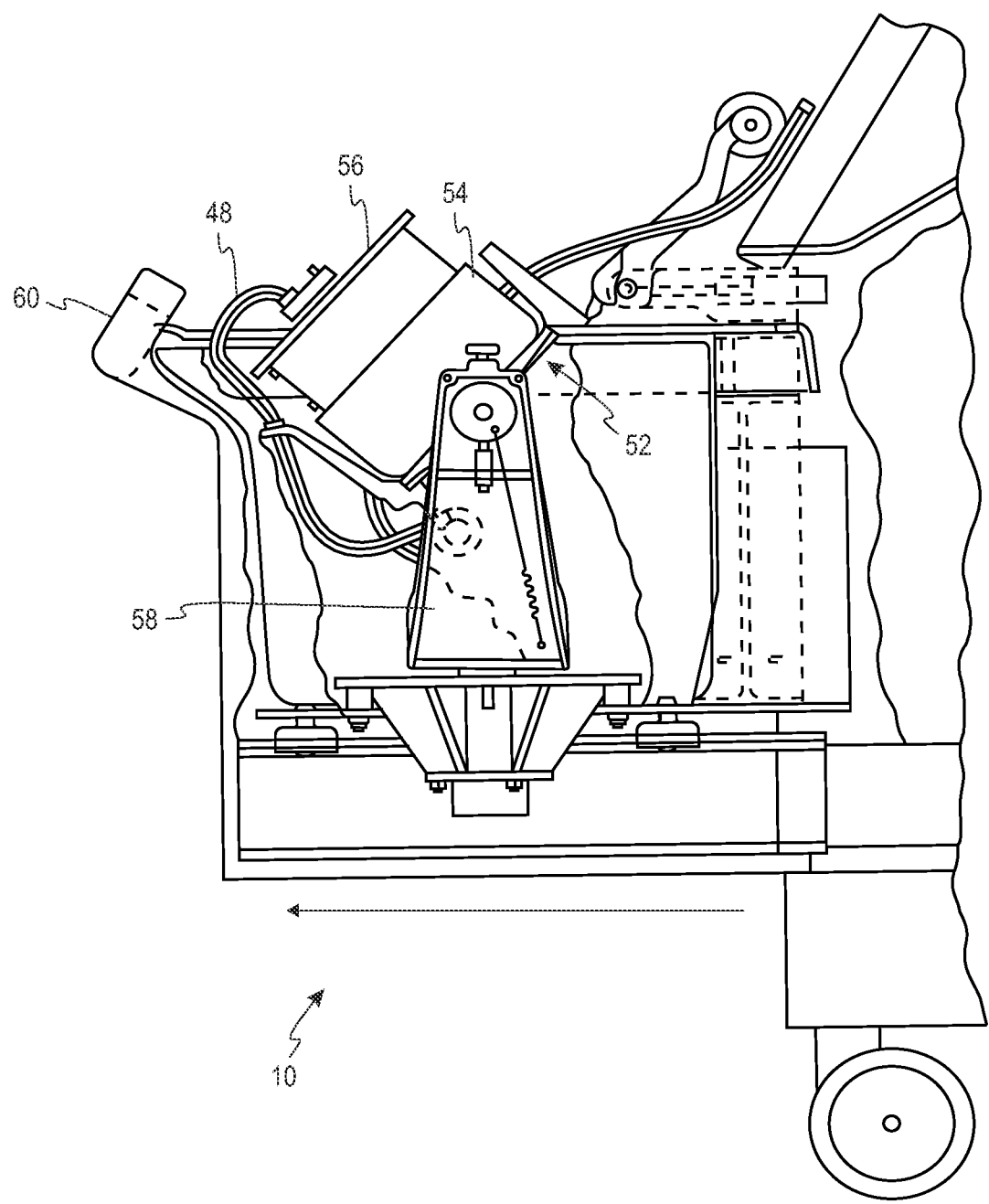
FIG. 4 is a side elevational view, with portions broken away and in section, of the fluid processing system of FIG. 1, with the centrifuge bowl and spool shown in an upright position for receiving a blood separation chamber.

As described above, the blood separation chamber 34 and the umbilicus 48 of the flow circuit 12 are loaded into the centrifuge 52, with a portion of the umbilicus 48 extending outside of the interior of the fluid processing system 10, as shown in FIG. 3. The sloped front panel 96 of the fluid processing system 10 includes at least one cassette holder 94 (three in the illustrated embodiment), each of which is configured to receive and grip an associated cassette 16-16*b* of the flow circuit 12. The cassettes are described in greater detail in U.S. Pat. No. 9,533,089, which is incorporated herein by reference.

Each of the cassette holders 94 receives and grips one of the cassettes 16-16*b* along the two opposed sides edges in the desired operating position. Each cassette holder 94 includes a pair of peristaltic pump stations 92. When each of the cassettes 16-16*b* is gripped by its respective cassette holder 94, tubing loops 50 extending from the cassettes 16-16*b* (FIG. 2) make operative engagement with the pump stations 92. The pump stations 92 are operated to cause fluid flow through the cassettes 16-16*b*.

As described above, the centrifuge 52 rotates the blood separation chamber 34, thereby centrifugally separating whole blood received from a blood source into component parts, e.g., red blood cells, plasma, and buffy coat comprising platelets and leukocytes.

During centrifugal separation, the blood separates into an optically dense layer containing cellular components, which forms as cellular components move under the influence of centrifugal force toward the high-G (outer) wall. The optically dense layer will be substantially comprised of red blood cells (and, hence, will be referred to herein as the "RBC layer") but, depending on the speed at which the centrifuge 52 is spun, other cellular components (e.g., larger white blood cells and platelets) may also be present in the RBC layer.

The movement of the component(s) of the RBC layer displaces less dense blood components radially toward the low-G (inner) wall, forming a second, less optically dense layer. The less optically dense layer is substantially comprised of plasma (and, hence, will be referred to herein as the "plasma layer") but, depending on the speed at which the centrifuge 52 is rotated and the length of time that the blood is resident in the centrifuge, other components (e.g., platelets and smaller white blood cells) may also be present in the plasma layer.

The transition between the formed cellular blood components and the liquid plasma component is generally referred to as the interface. Accordingly, where separation is achieved by centrifugation, the system may include an interface detecting unit that monitors the location of the interface. The interface detection unit may be of the type described in U.S. Pat. No. 6,027,657, incorporated herein by reference. As described in U.S. Pat. No. 6,027,657, a ramp may be provided in combination with a light source and a light detector to determine the radial position of the interface between RBC layer and the plasma layer.

As noted above, the ability to determine the interface between the RBC layer and the plasma layer is important for achieving efficient separation, and if the whole blood being separated is moderately or highly lipemic, or if the medications that the patient is taking has an impact on plasma clarity, the plasma becomes cloudy, making it difficult for the optical sensors to identify the separation interface.

Thus, in order to more clearly define the interface between the RBC layer and the plasma layer, a volume of saline is added to the whole blood to be separated prior to its introduction into the centrifugal separation chamber.

More specifically, with reference to FIG. 2, whole blood is flowed from the access device 14 to the separation chamber 34 through tubing 62 (from the access device 14 to the flow control cassette 16) and tubing 32 (from the flow control cassette 16 to the separation chamber 34), such that tubing 62, cassette 16 and tubing 32 generally comprise a "first tubing" connecting the access device to the separation chamber.

A volume of saline is added to the whole blood as it is flowed to the separation chamber 34. With reference to FIG. 2, a container of saline is attached to the access device 30, and saline is flowed from the container through tubing 64 to the flow control cassette 16, where the saline is combined with the whole blood that has been flowed to the cassette 16, such that the tubing 64 and the cassette 16 generally comprise a "second tubing" for flowing saline from the saline container to the "first tubing."

The volume of saline being added to the whole blood is tracked. To this end, one of the peristaltic pumps 92 may be associated with the second tubing so that the volume of saline being added to dilute the whole blood may be tracked by counting the number of pump strokes, with the volume of fluid that is pumped per stroke being known. Alternatively or additionally, the saline container may be supported by a weigh scale, and the volume of saline being added to dilute the whole blood may be tracked by monitoring the change in weight of the saline container.

The saline diluted whole blood is flowed to the separation chamber, where the whole blood is centrifuged to separate the whole blood into layers based on the density of its various cellular and non-cellular components, with an interface being formed between the different layers. In particular, such an interface is formed between the plasma and added saline and the cellular components of the whole blood. With the plasma and added saline so separated, it may be flowed from the separation chamber 34 through tubing 38, cassette 16*a* and tubing 46 to the collection container 44. The volume of the plasma and added saline in the collection container 44 is determined by, e.g., a weigh scale associated with the container 44. The volume of plasma in the collection container may be determined by taking the difference the total volume of plasma and added saline in the collection container 44 and the tracked volume of saline used for diluting the whole blood, which may be determined as discussed above.

Through experimentation, it may be determined that in order to have a suitable interface between the plasma and cellular components of the whole blood, the whole blood should have a specified hematocrit. Under such circumstances, the hematocrit of the whole blood that is to be separated may be determined and, based thereon, the volume of saline needed to dilute the whole blood to the specified hematocrit also determined, a that volume of saline is added to the whole blood prior to separation.

Alternatively, the amount of saline to be added to achieve the desired interface may be determined by performing a preliminary separation step in which undiluted whole blood is flowed to the separation chamber and separated by centrifugation so that an interface is established between the plasma and the cellular components of the whole blood. The quality of the interface may then be evaluated (i.e., whether a sufficiently distinct demarcation is presented between the cellular components and the plasma) by means of a detector for sensing the interface associated with the separation chamber or the level of transmittance of the resulting plasma or the top panel optical sensor may be used to compare optical readings of plasma throughout the procedure to evaluate the level of dilution achieved and to automatically make adjustments based on changes of optical sensor readings, and the volume of saline to be added to the whole blood subsequently flowed to the separation chamber is based thereon. This process could then be repeated, subject to allowable safety monitoring or operator defined limits, until sufficient demarcation is present to allow the procedure to continue with a clearly defined interface, or saline could be added regularly to maintain interface quality for the remainder of the procedure.

By way of the foregoing systems and methods for automatic dilution, changes in donor parameters, such as hematocrit or total blood volume, procedure endpoint targeting, and predicted procedure outputs for the patient, may be automatically accounted for. For example, at the start of the procedure, the operator is required to enter the starting hematocrit and total blood volume of the patient/donor. When auto-dilution occurs, the amount of saline added to the system, the amount of saline sent to the waste container, and the amount of saline returned to the patient/donor can be tracked. Thus, the patient's/donor's hematocrit and total blood volume at the end of the procedure may be accurately calculated. Further, for endpoint targeting, typically only the amount of separated plasma is tracked as an endpoint. With auto-dilution, the amount of saline mixed with the plasma is tracked so that a new procedure endpoint is established. If auto-dilution does not occur, the predicted procedure outputs established at the start of the procedure would be unchanged.

Various of the steps described above are susceptible to being performed automatically due to the system including a programmable controller. For example, the controller may be programmed or configured so that it: i) operates the first pump to flow saline from the container of saline through the second tubing segment to the first tubing segment to dilute the whole blood flowing through the first tubing segment, ii) tracks a volume of saline flowed from the container of saline through the second tubing segment to the first tubing segment, and iii) flows separated plasma and added saline from the separation chamber through the third tubing segment to the collection container, and iv) determines a volume for the plasma and added saline in the collection container. The controller may additionally be configured to determine the tracked volume of saline based on a signal received from a weigh scale and/or counting a number of pump strokes, and/or to determine the volume of plasma in the collection container based on the tracked volume of plasma added to the whole blood.

Aspects of the present subject matter described above may be beneficial alone or in combination with one or more other aspects. Without limiting the foregoing description, in accordance with one aspect of the subject matter herein, there is provided a method for centrifugally separating plasma from whole blood. The method comprises: a) introducing whole blood into a flow circuit having a blood access device connected to a first tubing for drawing whole blood from a blood source and for flowing whole blood to a centrifugal separation chamber; b) adding a volume of saline to the whole blood as it flows through the first tubing to dilute the whole blood; c) tracking the volume of saline added to the whole blood; d) separating the whole blood having the volume of saline added thereto in the centrifugal separation chamber whereby an interface is created between the plasma and added saline and the cellular components of the whole blood; e) flowing the separated plasma and added saline from the centrifugal separation chamber to a collection container; and f) determining a volume for the plasma and added saline in the collection container.

In a second aspect, the method further comprises determining a hematocrit for the whole blood prior to introducing whole blood into the first tubing and adding a volume of saline in an amount sufficient to dilute the whole blood to a predetermined hematocrit.

In a third aspect, the method further comprises flowing saline from a container of saline to the first tubing through second tubing.

In a fourth aspect, the second tubing has a peristaltic pump associated therewith, and the volume of saline added to the whole blood is tracked by counting pump strokes.

In a fifth aspect; the container of saline has a weigh scale associated therewith and the volume of saline added to the whole blood is tracked by the weigh scale.

In a sixth aspect, the volume of plasma in the collection container is determined based on the tracked volume of saline added to the whole blood.

In a seventh aspect, anticoagulant is added to the whole blood prior to its introduction into the separation chamber.

In an eighth aspect, a volume of whole blood is flowed through the first tubing to the centrifugal separation chamber prior to adding the volume of saline; the whole blood not having the volume of saline added thereto is separated in the centrifugal separation chamber so that an interface is created between the plasma and the cellular components of the whole blood; and the interface is evaluated to determine the volume of saline to be added to the whole blood subsequently flowed through the first tubing.

In a ninth aspect, a device for separating plasma from whole blood is provided comprising: a) a reusable hardware component comprising a centrifuge, an interface detector associated with the centrifuge, at least one pump, a first weigh scale, a second weigh scale, and a programmable controller for automatically operating the device; b) a single-use fluid flow circuit mounted to the reusable hardware component comprising a blood source access device, a separation chamber configured to be received in the centrifuge, first tubing segment connected on a first end to the blood source access device and on a second end to the separation chamber, a container of saline supported by the first weigh scale, a second tubing segment associated with the pump connected on a first end to the container of saline and on a second end to the first tubing segment, a collection container supported by the second weigh scale, and a third tubing segment connected on a first end to the separation chamber and on a second end to the collection container. The programmable controller is configured to: i) operate the first pump to flow saline from the container of saline through the second tubing segment to the first tubing segment to dilute the whole blood flowing through the first tubing segment, ii) track a volume of saline flowed from the container of saline through the second tubing segment to the first tubing segment, and iii) flow separated plasma and added saline from the separation chamber through the third tubing segment to the collection container, and iv) determine a volume for the plasma and added saline in the collection container.

In a tenth aspect, the reusable hardware component further comprises a hematocrit detector associated with the first tubing segment for determining the hematocrit of whole blood flowing through the first tubing segment and the programmable controller is further configured to: determine a hematocrit for the whole blood prior to introducing whole blood into the first tubing and add a volume of saline in an amount sufficient to dilute the whole blood to a predetermined hematocrit.

In an eleventh aspect, the programmable controller is configured to determine the tracked volume of saline added to the whole blood based on a signal received from the weigh scale.

In a twelfth aspect, the pump is a peristaltic pump and the programmable controller is configured to determine the tracked volume of saline added to the whole blood based on counting a number of pump strokes.

In a thirteenth aspect, the programmable controller is further configured to determine the volume of plasma in the collection container based on the tracked volume of saline added to the whole blood.

In a fourteenth aspect, the reusable hardware component further comprises a detector for sensing an interface created between the plasma and cellular components of the whole blood and the programmable controller is further configured to: flow a volume of whole blood through the first tubing to the separation chamber prior to adding the volume of saline; separate the whole blood not having the volume of saline added thereto in the separation chamber to create in interface between the plasma and the cellular components of the whole blood, and to evaluate the interface based on a signal received from the interface detector to determine the volume of saline to be added to the whole blood flowed through the first tubing.

The invention claimed is:

1. A device for separating plasma from whole blood including turbid plasma comprising:
   a) a reusable hardware component comprising a centrifuge, an interface detector associated with the centrifuge, at least one pump, a first weigh scale, a second weigh scale, and a programmable controller for automatically operating the device;
   b) a single-use fluid flow circuit mounted to the reusable hardware component, wherein the single-use fluid flow circuit comprises a blood source access device, a separation chamber configured to be received in the centrifuge, a first tubing segment connected on a first end to the blood source access device and on a second end to the separation chamber, a container of saline supported by the first weigh scale, a second tubing segment associated with the at least one pump connected on a first end to the container of saline and on a second end to the first tubing segment, a collection container supported by the second weigh scale, and a third tubing segment connected on a first end to the separation chamber and on a second end to the collection container; and
   c) wherein the programmable controller is configured to: i) prime the single-use fluid flow circuit with saline from the container of saline, ii) flow a volume of the whole blood including turbid plasma through the first tubing segment to the separation chamber prior to adding a volume of additional saline; separate the whole blood including turbid plasma in the separation chamber to create a definable interface between the separated plasma and cellular components of the whole blood; evaluate the definable interface based on a signal received from the interface detector to determine a volume of saline to be added to the whole blood including turbid plasma flowed through the first tubing segment; iii) operate the at least one pump to flow the volume of additional saline from the container of saline through the second tubing segment to the whole blood including turbid plasma that is collected directly from a donor and that is flowing through the first tubing segment, the volume of additional saline being flowed to dilute the whole blood including turbid plasma and to arrive at a predetermined hematocrit to establish the definable interface after separation of the whole blood including turbid plasma in the separation chamber between (a) a layer including the turbid plasma mixed with the volume of additional saline and (b) a cellular component layer, iv) direct flow of the diluted whole blood including turbid plasma to the separation chamber, v) track the volume of additional saline flowed from the container of saline through the second tubing segment to the first tubing segment, wherein said volume of additional saline comprises a tracked volume of saline, vi) flow the separated plasma and the saline from the separation chamber through the third tubing segment to the collection container, and vii) determine a volume for the separated plasma and the saline in the collection container.

2. The device of claim 1 wherein the reusable hardware component further comprises a hematocrit detector associated with the first tubing segment for determining a hematocrit of the whole blood including turbid plasma flowing through the first tubing segment and the programmable controller is further configured to: determine the hematocrit for the whole blood including turbid plasma prior to introducing the whole blood including turbid plasma into the first tubing segment and add a volume of saline in an amount sufficient to dilute the whole blood including turbid plasma to the predetermined hematocrit.

3. The device of claim 1 wherein the programmable controller is configured to determine the tracked volume of saline added to the whole blood including turbid plasma based on a signal received from the first weigh scale.

4. The device of claim 1 wherein the at least one pump includes a peristaltic pump and the programmable controller is configured to determine the tracked volume of saline added to the whole blood including turbid plasma based on counting a number of pump strokes.

5. The device of claim 1 wherein the programmable controller is further configured to determine the volume of the separated plasma in the collection container by using the tracked volume of saline added to the whole blood including turbid plasma.

6. The device of claim 3 wherein the programmable controller is further configured to determine the volume of the separated plasma in the collection container based on the tracked volume of saline added to the whole blood including turbid plasma.

7. The device of claim 4 wherein the programmable controller is further configured to determine the volume of the separated plasma in the collection container based on the tracked volume of saline added to the whole blood including turbid plasma.

8. The device of claim 1, wherein the programmable controller is configured to flow the volume of additional saline from the container of saline through the second tubing segment to the first tubing segment to arrive at a selected hematocrit of the whole blood including turbid plasma flowing through the first tubing segment to define the definable interface.

9. A device for separating plasma from whole blood comprising:
a) a reusable hardware component comprising a centrifuge, an interface detector associated with the centrifuge, at least one pump, a first weigh scale, a second weigh scale, and a programmable controller for automatically operating the device;
b) a single-use fluid flow circuit mounted to the reusable hardware component, wherein the single-use fluid flow circuit comprises a blood source access device, a separation chamber configured to be received in the centrifuge, a first tubing segment connected on a first end to the blood source access device and on a second end to the separation chamber, a container of saline supported by the first weigh scale, a second tubing segment associated with the at least one pump connected on a first end to the container of saline and on a second end to the first tubing segment, a collection container supported by the second weigh scale, and a third tubing segment connected on a first end to the separation chamber and on a second end to the collection container; and
c) wherein the programmable controller is configured to:
i) flow a volume of whole blood through the first tubing segment to the separation chamber prior to adding a volume of saline, ii) separate the volume of whole blood in the separation chamber to create a definable interface between the separated plasma and cellular components of the whole blood, iii) evaluate the definable interface based on a signal received from the interface detector to determine the volume of saline to be added to subsequent whole blood flowed through the first tubing segment if during evaluation the definable interface is not sensed, and to add the determined volume of saline to the subsequent whole blood to establish the definable interface after separation of the subsequent whole blood, iv) operate the at least one pump to flow the determined volume of saline from the container of saline to the separation chamber, v) track the volume of saline flowed from the container of saline to the separation chamber, wherein said volume of saline comprises a tracked volume of saline, vi) flow the separated plasma and saline from the separation chamber through the third tubing segment to the collection container, and vii) determine a volume for the separated plasma and the saline in the collection container.

10. The device of claim 9 comprising repeating steps (iii)-(v).

* * * * *